(12) United States Patent
Ratner

(10) Patent No.: US 8,256,414 B2
(45) Date of Patent: Sep. 4, 2012

(54) NEONATAL COLORIMETRIC CARBON DIOXIDE DETECTOR

(75) Inventor: Jeffrey B. Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 539 days.

(21) Appl. No.: 12/472,011

(22) Filed: May 26, 2009

(65) Prior Publication Data

US 2010/0305464 A1  Dec. 2, 2010

(51) Int. Cl.
- A61M 15/00  (2006.01)
- A61M 16/00  (2006.01)
- A62B 7/00  (2006.01)
- G01J 1/48  (2006.01)

(52) U.S. Cl. ............... 128/200.24; 128/205.23; 422/86

(58) Field of Classification Search ............ 128/207.17, 128/205.23, 200.24; 422/86
See application file for complete search history.

(56) References Cited

U.S. PATENT DOCUMENTS

| | | | | |
|---|---|---|---|---|
| 4,205,043 A * | 5/1980 | Esch et al. | ................. | 422/416 |
| 4,211,239 A * | 7/1980 | Raemer et al. | ................. | 600/529 |
| 4,879,999 A * | 11/1989 | Leiman et al. | ................. | 128/207.14 |
| 5,005,572 A * | 4/1991 | Raemer et al. | ................. | 128/207.14 |
| 5,197,464 A * | 3/1993 | Babb et al. | ................. | 128/207.14 |
| 5,273,029 A * | 12/1993 | Wilk et al. | ................. | 128/200.26 |
| 5,291,879 A * | 3/1994 | Babb et al. | ................. | 128/200.26 |
| 5,375,592 A * | 12/1994 | Kirk et al. | ................. | 128/207.14 |
| 5,468,451 A * | 11/1995 | Gedeon | ................. | 422/416 |
| 5,765,550 A * | 6/1998 | Psaros et al. | ................. | 128/202.27 |
| 5,846,836 A * | 12/1998 | Mallow | ................. | 436/169 |
| 5,965,061 A * | 10/1999 | Larsson et al. | ................. | 252/408.1 |
| 6,144,869 A * | 11/2000 | Berner et al. | ................. | 600/347 |
| 6,187,596 B1 * | 2/2001 | Dallas et al. | ................. | 436/169 |
| 6,378,522 B1 * | 4/2002 | Pagan | ................. | 128/207.14 |
| 6,502,573 B1 * | 1/2003 | Ratner | ................. | 128/207.17 |
| 2010/0310425 A1 * | 12/2010 | Piper | ................. | 422/86 |

OTHER PUBLICATIONS

Aziz et al., The pediatric disposable end-tidal carbon dioxide detector role in endotracheal intubation in newborns. J.of Perinatology 19(2) : 110 (1999).*

Cardoso et al., Portable devices used to detect endotracheal intubation during emergency situations: a review. Critical Care Medicine 26(5) : 957 (1998).*

Garey et al., Tidal volume threshold for colorimetric carbon dioxide detectors available for use in neonates. Pediatrics 121 : e1524 (Jun. 2008).*

* cited by examiner

Primary Examiner — Ethan C Whisenant
(74) Attorney, Agent, or Firm — Larson & Larson, P.A.; Frank Liebenow; Justin Miller

(57) ABSTRACT

An application for a neonatal calorimetric carbon dioxide detector has a calorimetric carbon dioxide detector membrane having a pH-sensitive chemical indicator that undergoes calorimetric change in the presence of carbon dioxide. The detector has a patient orifice in fluid communication with the baby's airway and a respiration equipment orifice connected to a breathing system. The patient orifice is connected to a breathing tube and when the breathing tube is inserted correctly into the trachea, as the baby exhales, carbon dioxide interacts with the calorimetric membrane which changes color based upon the concentration of carbon dioxide. The neonatal calorimetric carbon dioxide detector adds a volume of less than or equal to 1 mL after being attached to a breathing circuit.

16 Claims, 4 Drawing Sheets

NEONATAL COLORIMETRIC CARBON DIOXIDE DETECTOR

FIELD OF THE INVENTION

The present invention relates in general to the field of calorimetric carbon dioxide detectors, particularly for use with low-birth weight neonatal patients.

BACKGROUND

Airway adapters are generally used with patients being given respiratory assistance, such as patients under anesthesia, or patients on life support systems, to connect between the patient airway (mouth, nose, tracheal tube) and a ventilating tube of a breathing apparatus. The ventilating tubes convey breathing gases to the patient and exhaled breath away from the patient (typically, the airway adapter is in the form of a short connector of tubular shape making a connection between the generally different cross sections of tubes).

End-tidal carbon dioxide ($ETCO_2$) detection provides a non-invasive indication of the proper insertion of the airway tube is obtained by the analysis of the exhaled breath gases. End-tidal carbon dioxide ($ETCO_2$) detection indicates to the clinician whether the airway tube is inserted correctly into the trachea. If inserted correctly, carbon dioxide is detected. If the airway tube is inserted incorrectly (into the esophagus), no carbon dioxide is detected and the clinician knows to remove the airway tube and reinsert it.

Airway components are typically made as plastic injection moldings, keeping production costs low. The amount of void volume (also known as dead space) in such airway components is typically very considerable. For neonatal applications, especially those with low birth weight, the patient has very little exhalation air volume. Airway adapters needs to have minimal added void volume to reduce the effects of gas mixing which would adversely affect the integrity of a calorimetric carbon dioxide detector membrane. Existing devices claim to have 3 mL of internal volume (dead space), when in actuality, these devices have 5 mL of internal volume before they are inserted into a circuit and 3 mL of internal volume after inserted into a circuit.

There exists a serious need for a sampling airway adapter for use with low birth weight neonatal patients, which overcomes the disadvantages of available adapters by reducing the internal volume to approximately 1 mL when inserted into a circuit and used with neonatal patients.

SUMMARY OF THE INVENTION

A neonatal calorimetric carbon dioxide detector has a calorimetric carbon dioxide detector membrane having a pH-sensitive chemical indicator that undergoes calorimetric change in the presence of carbon dioxide. The detector has a patient orifice in fluid communication with the baby's airway and a respiration equipment orifice connected to a breathing system. The patient orifice is connected to a breathing tube and when the breathing tube is inserted correctly into the trachea, as the baby exhales, carbon dioxide interacts with the calorimetric membrane which changes color based upon the concentration of carbon dioxide. The total internal volume of the neonatal calorimetric carbon dioxide detector is less than or equal to 3.8 mL before being attached to a breathing circuit and the neonatal calorimetric carbon dioxide detector adds less than or equal to 1 mL to a breathing circuit after being inserted.

In one embodiment, a neonatal calorimetric carbon dioxide detector is disclosed including an enclosure having a patient orifice in fluid communication with a patient's airway and a respiration equipment orifice. The respiration equipment orifice is also in fluid communication with the patient orifice. A calorimetric membrane is held within the enclosure and visible from outside of the enclosure. The calorimetric membrane is situated such that exhalation gas from the patient orifice passes around and/or through the calorimetric membrane before leaving the respiration equipment orifice. The total internal volume of the enclosure is less than or equal to 3.8 mL before being attached to a breathing circuit and the neonatal calorimetric carbon dioxide detector adds less than or equal to 1 mL to a breathing circuit after being inserted.

In another embodiment, a neonatal calorimetric carbon dioxide detector is disclosed including a patient orifice in fluid communication with a patient's airway and a respiration equipment orifice in fluid communication with the respiration equipment orifice. A bottom surface of the respiration equipment orifice is affixed to a top surface of the patient orifice. A calorimetric membrane is held between the respiration equipment orifice and the patient orifice. The calorimetric membrane is in fluid communication with the patient orifice such that exhalation gas from the patient orifice passes through and around the calorimetric membrane before leaving out of the respiration equipment orifice. For neonatal application in patients of low birth weight, The total internal volume of the respiration equipment orifice and the patient orifice is less than or equal to 3.8 mL before being attached to a breathing circuit and the neonatal calorimetric carbon dioxide detector adds less than or equal to 1 mL to a breathing circuit after being inserted.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
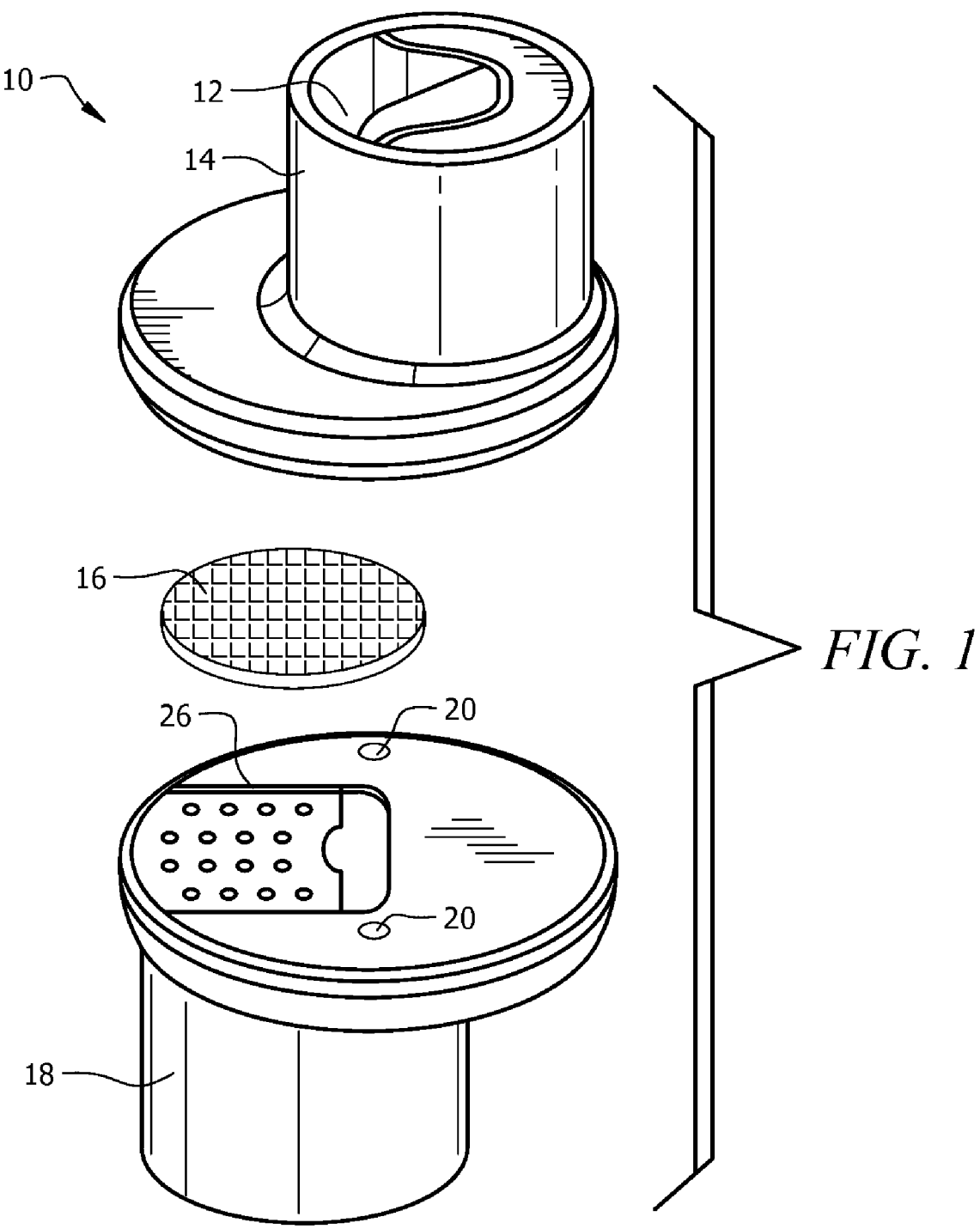
FIG. 1 illustrates a perspective view of a neonatal calorimetric carbon dioxide detector of the present invention.

Reference will now be made in detail to the presently preferred embodiments of the invention, examples of which are illustrated in the accompanying drawings. Throughout the following detailed description, the same reference numerals refer to the same elements in all figures.

The present invention discloses a neonatal calorimetric carbon dioxide detector 10 suited for low birth weight neonatal patients (low birth weight babies are often classified as those who weigh less than 2.5 kg).

Figure 2:
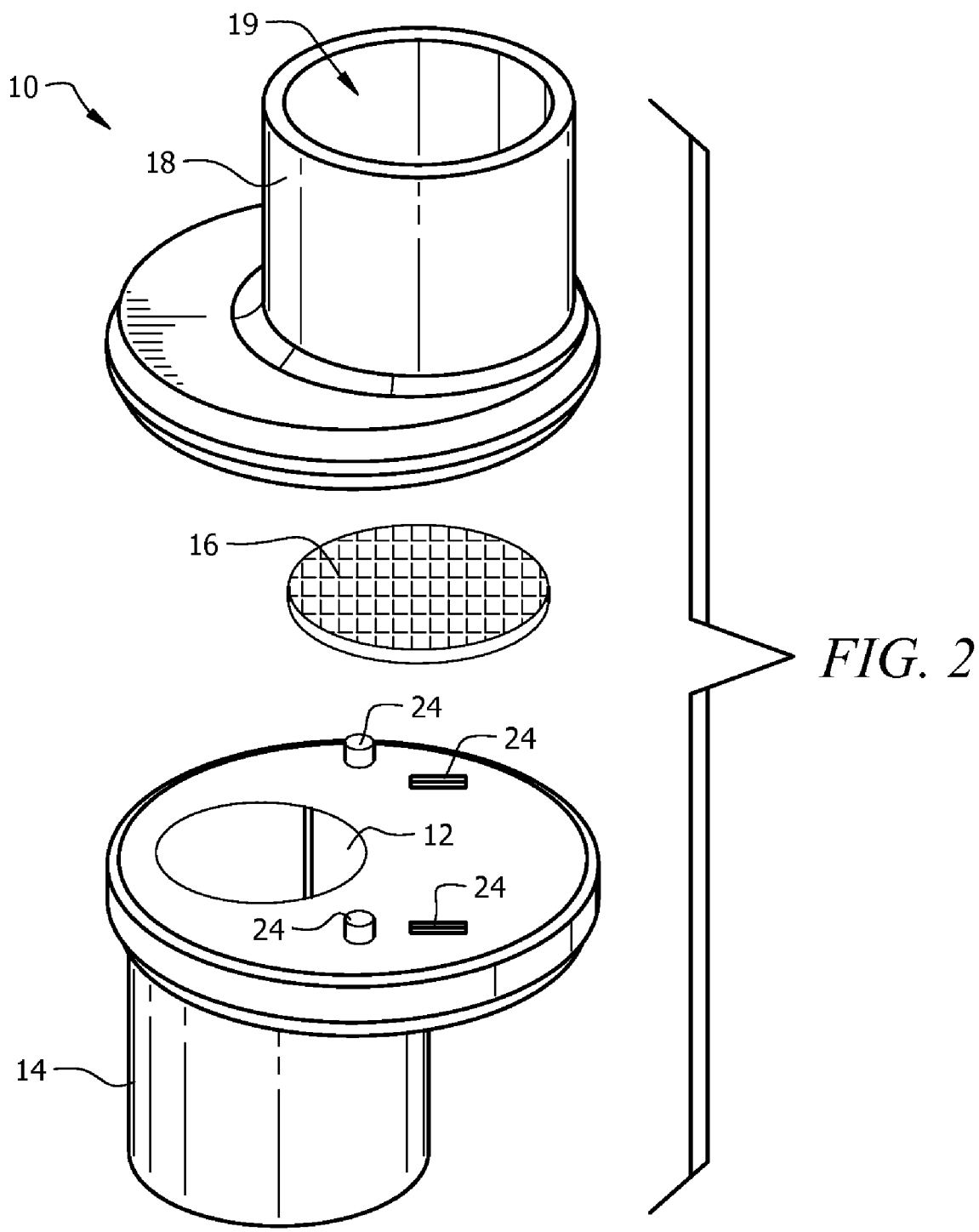
FIG. 2 illustrates a second perspective view of a neonatal calorimetric carbon dioxide detector of the present invention.

Referring to FIGS. 1 and 2, top and bottom perspective views of a neonatal calorimetric carbon dioxide detector 10 of the present invention are shown. Although one specific method of fabrication and construction of the neonatal calorimetric carbon dioxide detector 10 is shown, many such methods and fabrication techniques are known and all are anticipated an included here within.

The example of FIGS. 1 and 2 includes a top molded section 14, a bottom molded section 18 and a calorimetric membrane 16. The top molded section 14 includes a respiration equipment orifice 12 for accepting air flow from a breathing device (e.g., a breathing bag or ventilation equipment, not shown). The bottom molded section 18 includes a patient orifice 19 for communicating with the patient. The top molded section 14 and the bottom molded section 18 form an enclosure 10 having a respiration equipment orifice 12 at the top and a patient orifice 19 at the opposite end.

The calorimetric membrane 16 is held on one side above a perforated grill section 26 and kept in place by, for example, two molded protrusions 24 on the inside surface of the top molded section 14. Although one specific method of fabrication and holding of the calorimetric membrane 16 in position while marrying the top molded section 14 to the bottom molded section 18 is shown, many such methods and fabrication techniques are known and all are anticipated an included here within. The calorimetric membrane 16 is situated in fluid communication with the air flow from the patient orifice 19 such that, as the patient exhales, the calorimetric membrane 16 is exposed to the exhaled gases as the exhaled gases pass around and/or through the calorimetric membrane 16. Therefore, the calorimetric membrane 16 will change color depending upon the presence and the concentration of the gas of interest (e.g., carbon dioxide). For example, one typical carbon dioxide calorimetric membrane 16 is blue when no $CO_2$ is present, green when 1% to 2% $CO_2$ is present, yellow/green when 2% to 5% $CO_2$ is present and yellow when more than 5% $CO_2$ is present. In another example, another typical carbon dioxide calorimetric membrane 16 is purple when less than 0.5% $CO_2$ is present, tan when 0.5% to 2% $CO_2$ is present, mustard yellow when 2% to 5% $CO_2$ is present and yellow when more than 5% $CO_2$ is present. To prevent exposure to the gas of interest before use, it is known to ship the neonatal calorimetric carbon dioxide detector 10 in a hermetically sealed container or bag.

There are many ways known to join the top molded section 14 and the bottom molded section 18, one of which is to have one or more pegs, posts or snaps 24 that fit into holes 20. The neonatal calorimetric carbon dioxide detector 10 is preferably made from a transparent or translucent material, making the calorimetric membrane 16 is visible from outside through a surface of the neonatal calorimetric carbon dioxide detector 10.

Figure 3:
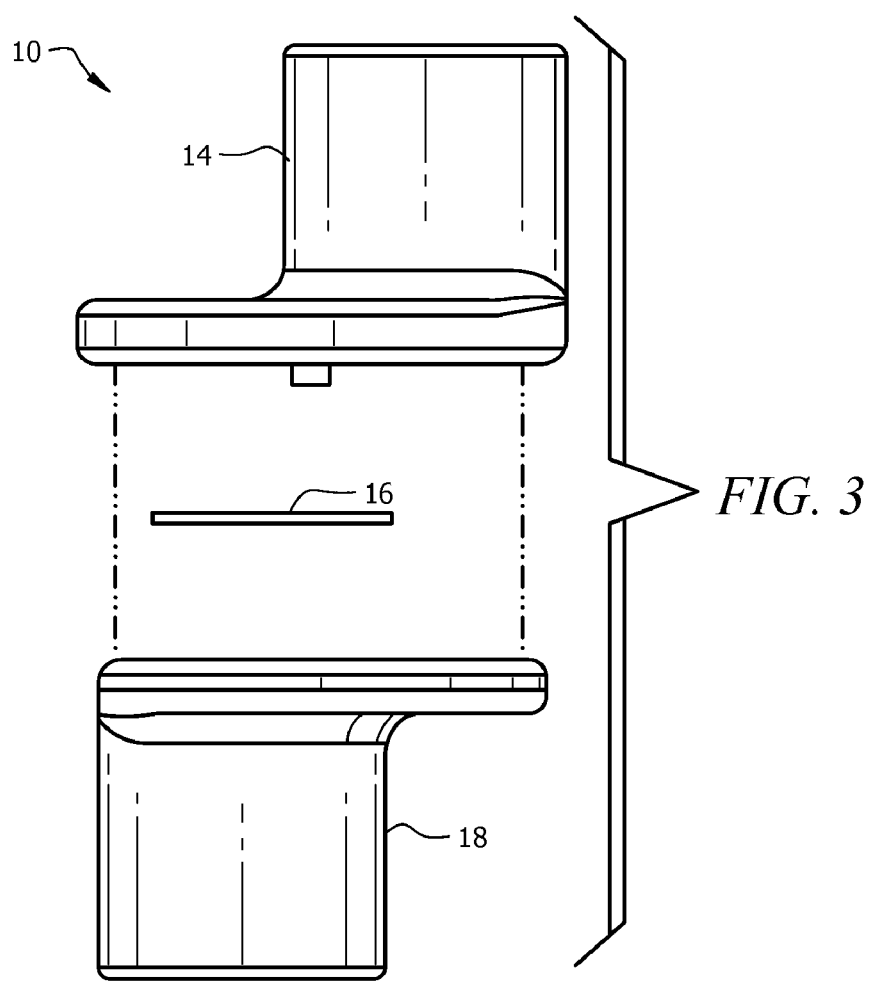
FIG. 3 illustrates a plan view of the neonatal calorimetric carbon dioxide detector of the present invention before assembly.

Referring to FIG. 3, a plan view of the neonatal calorimetric carbon dioxide detector 10 is shown before assembly. Shown, is the relationship of the top molded section 14 and the bottom molded section 18 with the calorimetric membrane 16 positioned to be held between the top molded section 14 and the bottom molded section 18. There are many ways known to join the top molded section 14 and the bottom molded section 18, one of which is to have one or more pegs, posts or snaps 24 that fit into holes 20, thereby holding the top molded section 14 and the bottom molded section 18 together with or without an adhesive. Other methods include the use of adhesives, ultrasonic welding, etc.

Figure 4:
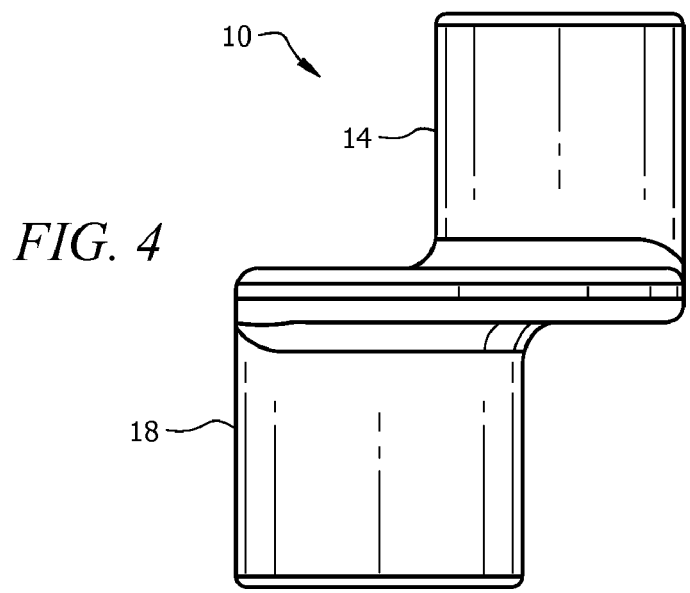
FIG. 4 illustrates a plan view of the neonatal calorimetric carbon dioxide detector of the present invention after assembly.

Referring to FIG. 4, a plan view of the present invention after assembly is shown. Once the top molded section 14 and the bottom molded section 18 of the neonatal calorimetric carbon dioxide detector 10 are assembled around the calorimetric membrane 16, the total internal air volume is approximately 3.8 mL or less than 3.8 mL. Insertion of the neonatal calorimetric carbon dioxide detector 10 into an airway circuit increases the total internal air volume 45 (see FIG. 5) by approximately 1 mL and preferably by less than 1 mL.

Figure 5:
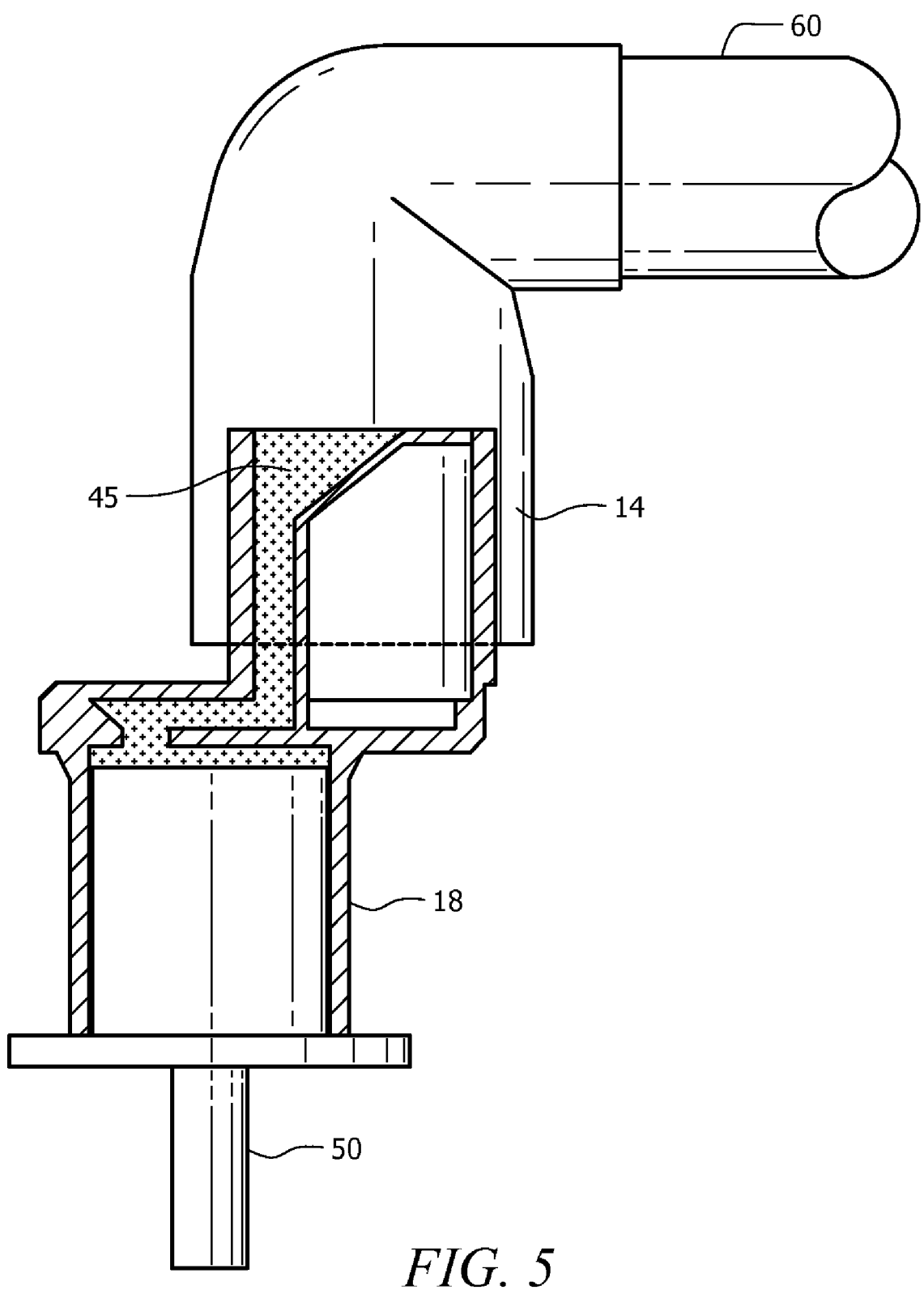
FIG. 5 illustrates a cross-sectional view of the neonatal calorimetric carbon dioxide detector of the present invention.

Referring to FIG. 5, a cross-sectional view of the present invention after assembly is shown. The neonatal calorimetric carbon dioxide detector top molded section 14 interfaces to respiration equipment through, for example, a gas tube 60. The bottom molded section 18 interfaces to the patient through, for example, a tracheal or endo-tracheal tube 50. The total internal air volume is approximately 3.8 mL or less than 3.8 mL. Insertion of the neonatal calorimetric carbon dioxide detector 10 into an airway circuit increases the total internal air volume 45 by approximately 1 mL and preferably by less than 1 mL.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A neonatal colorimetric carbon dioxide detector, the neonatal colorimetric carbon dioxide detector formed to insert into an airway circuit, the neonatal colorimetric carbon dioxide detector comprising:
    an enclosure having a patient orifice in fluid communication with a patient's airway and a respiration equipment orifice, the respiration equipment orifice in fluid communication with the patient orifice, the respiration equipment orifice being partially occluded thereby reducing an internal volume of the respiration equipment orifice; and
    a colorimetric membrane held within the enclosure and visible from outside of the enclosure, the colorimetric membrane in fluid communication with the patient orifice such that the colorimetric membrane is exposed to exhalation gas from the patient orifice before the exhalation gas exits through the respiration equipment orifice;
    whereas insertion of the neonatal colorimetric carbon dioxide detector into the airway circuit increases a total internal volume of the airway circuit by less than or equal to 1 mL.

2. The neonatal colorimetric carbon dioxide detector of claim 1, wherein the colorimetric membrane changes color in response to exposure to carbon dioxide gas.

3. The neonatal colorimetric carbon dioxide detector of claim 1, wherein the total internal volume of the enclosure is 3.8 mL and insertion of the neonatal colorimetric carbon dioxide detector into the airway circuit increases the total internal volume of the airway circuit by 1 mL.

4. The neonatal colorimetric carbon dioxide detector of claim 2, wherein the colorimetric membrane changes color from blue to green in response to exposure to exhalation gas having 1% to 2% of carbon dioxide gas.

5. The neonatal colorimetric carbon dioxide detector of claim 2, wherein the colorimetric membrane changes color to yellow/green in response to exposure to exhalation gas having 2% to 5% of carbon dioxide gas.

6. The neonatal colorimetric carbon dioxide detector of claim 2, wherein the colorimetric membrane changes color to yellow in response to exposure to exhalation gas having greater than 5% of carbon dioxide gas.

7. A neonatal colorimetric carbon dioxide detector with carbon dioxide detection, the neonatal colorimetric carbon dioxide detector formed to insert into an airway circuit, the neonatal colorimetric carbon dioxide detector comprising:
an enclosure having a patient orifice in communication with a patient's airway and a respiration equipment orifice, the respiration equipment orifice in fluid communication with the patient orifice, the respiration equipment orifice connected to the patient orifice by two pegs on a bottom surface of the respiration equipment orifice mating with two holes on a top surface of the patient orifice, the respiration equipment orifice being partially occluded thereby reducing an internal volume of the respiration equipment orifice; and
a colorimetric membrane held within the enclosure and visible through the enclosure, the colorimetric membrane in fluid communication with the patient orifice such that the colorimetric membrane is exposed to exhalation gas from the patient orifice before the exhalation gas exits through the respiration equipment orifice;
whereas a total internal volume of the enclosure is 3.8 mL before the neonatal colorimetric carbon dioxide detector is inserted into the airway circuit and the neonatal colorimetric carbon dioxide detector adds less than or equal to 1 mL to the airway circuit after the neonatal colorimetric carbon dioxide detector is inserted into the airway circuit.

8. The neonatal colorimetric carbon dioxide detector of claim 7, wherein the colorimetric membrane changes color in response to exposure to carbon dioxide gas.

9. The neonatal colorimetric carbon dioxide detector of claim 8, wherein the colorimetric membrane changes color from blue to green in response to exposure to exhalation gas having 1% to 2% of carbon dioxide gas.

10. The neonatal colorimetric carbon dioxide detector of claim 8, wherein the colorimetric membrane changes color to yellow/green in response to exposure to exhalation gas having 2% to 5% of carbon dioxide gas.

11. The neonatal colorimetric carbon dioxide detector of claim 8, wherein the colorimetric membrane changes color to yellow in response to exposure to exhalation gas having greater than 5% of carbon dioxide gas.

12. A neonatal colorimetric carbon dioxide detector with carbon dioxide detection, the neonatal colorimetric carbon dioxide detector formed to insert into an airway circuit of a low birth weight neonatal patient, the neonatal colorimetric carbon dioxide detector comprising:
a patient orifice in fluid communication with a patient's airway;
a respiration equipment orifice in fluid communication with the patient orifice, a bottom circumferential edge of the respiration equipment orifice interfaced to and overlapping a top circumferential edge of the patient orifice, the respiration equipment orifice being partially occluded thereby reducing an internal volume of the respiration equipment orifice; and
a colorimetric membrane held between the respiration equipment orifice and the patient orifice, the colorimetric membrane is visible through the respiration equipment orifice, the colorimetric membrane in fluid communication with the patient orifice such that the colorimetric membrane is exposed to exhalation gas from the patient orifice before the exhalation gas exits through the respiration equipment orifice;
whereas a total internal volume of the respiration equipment orifice and the patient orifice is less than or equal to 3.8 mL before the neonatal colorimetric carbon dioxide detector is inserted into the airway circuit and the neonatal colorimetric carbon dioxide detector adds less than or equal to 1 mL after the neonatal colorimetric carbon dioxide detector is inserted into the airway circuit.

13. The neonatal colorimetric carbon dioxide detector of claim 12, wherein the colorimetric membrane changes color in response to exposure to carbon dioxide gas.

14. The neonatal colorimetric carbon dioxide detector of claim 13, wherein the colorimetric membrane changes color from blue to green in response to exposure to exhalation gas having 1% to 2% of carbon dioxide gas.

15. The neonatal colorimetric carbon dioxide detector of claim 13, wherein the colorimetric membrane changes color to yellow/green in response to exposure to exhalation gas having 2% to 5% of carbon dioxide gas.

16. The neonatal colorimetric carbon dioxide detector of claim 13, wherein the colorimetric membrane changes color to yellow in response to exposure to exhalation gas having greater than 5% of carbon dioxide gas.

* * * * *

UNITED STATES PATENT AND TRADEMARK OFFICE
CERTIFICATE OF CORRECTION

PATENT NO. : 8,256,414 B2  
APPLICATION NO. : 12/472011  
DATED : September 4, 2012  
INVENTOR(S) : Jeffrey B. Ratner It is certified that error appears in the above-identified patent and that said Letters Patent is hereby corrected as shown below:

On the Title Page

1. Abstract, Line 1 - change calorimetric to colorimetric
2. Abstract, Line 2 - change calorimetric to colorimetric
3. Abstract, Line 4 - change calorimetric to colorimetric
4. Abstract, Line 10 - change calorimetric to colorimetric
5. Abstract, Line 12 - change calorimetric to colorimetric In the Specifications 6. Column 1, Line 7 - change calorimetric to colorimetric
7. Column 1, Line 38-39 - change calorimetric to colorimetric
8. Column 1, Line 52 - change calorimetric to colorimetric
9. Column 1, Line 52-53 - change calorimetric to colorimetric
10. Column 1, Line 54 - change calorimetric to colorimetric
11. Column 1, Line 61 - change calorimetric to colorimetric
12. Column 1, Line 63 - change calorimetric to colorimetric
13. Column 1, Line 65 - change calorimetric to colorimetric
14. Column 2, Line 1 - change calorimetric to colorimetric
15. Column 2, Line 6 - change calorimetric to colorimetric
16. Column 2, Line 7 - change calorimetric to colorimetric
17. Column 2, Line 9 - change calorimetric to colorimetric
18. Column 2, Line 13 - change calorimetric to colorimetric
19. Column 2, Line 15 - change calorimetric to colorimetric
20. Column 2, Line 21 - change calorimetric to colorimetric
21. Column 2, Line 22 - change calorimetric to colorimetric
22. Column 2, Line 25 - change calorimetric to colorimetric
23. Column 2, Line 30 - change calorimetric to colorimetric
24. Column 2, Line 40-41 - change calorimetric to colorimetric Signed and Sealed this  
Twentieth Day of August, 2013

Teresa Stanek Rea  
*Acting Director of the United States Patent and Trademark Office*

CERTIFICATE OF CORRECTION (continued)
U.S. Pat. No. 8,256,414 B2

25. Column 2, Line 43 - change calorimetric to colorimetric
26. Column 2, Line 44 - change calorimetric to colorimetric
27. Column 2, Line 47 - change calorimetric to colorimetric
28. Column 2, Line 51 - change calorimetric to colorimetric
29. Column 2, Line 60 - change calorimetric to colorimetric
30. Column 2, Line 65 - change calorimetric to colorimetric
31. Column 2, Line 67 to Column 3, Line 1 - change calorimetric to colorimetric
32. Column 3, Line 5 - change calorimetric to colorimetric
33. Column 3, Line 14 - change calorimetric to colorimetric
34. Column 3, Line 18 - change calorimetric to colorimetric
35. Column 3, Line 22 - change calorimetric to colorimetric
36. Column 3, Line 24 - change calorimetric to colorimetric
37. Column 3, Line 26 - change calorimetric to colorimetric
38. Column 3, Line 27 - change calorimetric to colorimetric
39. Column 3, Line 30 - change calorimetric to colorimetric
40. Column 3, Line 34 - change calorimetric to colorimetric
41. Column 3, Line 39 - change calorimetric to colorimetric
42. Column 3, Line 44 - change calorimetric to colorimetric
43. Column 3, Line 46 - change calorimetric to colorimetric
44. Column 3, Line 47 - change calorimetric to colorimetric
45. Column 3, Line 49-50 - change calorimetric to colorimetric
46. Column 3, Line 52 - change calorimetric to colorimetric
47. Column 3, Line 63 - change calorimetric to colorimetric
48. Column 3, Line 64-65 - change calorimetric to colorimetric
49. Column 3, Line 67 - change calorimetric to colorimetric
50. Column 4, Line 4 - change calorimetric to colorimetric
51. Column 4, Line 10 - change calorimetric to colorimetric